(12) United States Patent
Herskovic

(10) Patent No.: US 8,459,602 B2
(45) Date of Patent: Jun. 11, 2013

(54) CLAMPING DEVICE

(76) Inventor: Arnold Herskovic, Chicago, IL (US)

( * ) Notice: Subject to any disclaimer, the term of this patent is extended or adjusted under 35 U.S.C. 154(b) by 95 days.

(21) Appl. No.: 12/780,274

(22) Filed: May 14, 2010

(65) Prior Publication Data

US 2011/0121149 A1 May 26, 2011

Related U.S. Application Data

(63) Continuation-in-part of application No. 11/419,248, filed on May 19, 2006, now Pat. No. 8,011,629.

(51) Int. Cl.
*A47B 96/06* (2006.01)

(52) U.S. Cl.
USPC ............... 248/230.1; 248/229.15; 248/229.13

(58) Field of Classification Search
USPC ................. 248/230.1, 229.15, 229.13; 16/29, 16/32
See application file for complete search history.

(56) References Cited

U.S. PATENT DOCUMENTS

| | | |
|---|---|---|
| 364,555 A | 6/1887 | Turly |
| 2,970,798 A | 2/1961 | Friotchle et al. |
| 3,709,372 A | 1/1973 | Alexander |
| D269,156 S | 5/1983 | Slinkard |
| 4,431,206 A | 2/1984 | Pryor |
| 4,511,157 A | 4/1985 | Wilt |
| 4,511,158 A | 4/1985 | Varga et al. |
| 4,572,536 A | 2/1986 | Doughty |
| 4,767,131 A | 8/1988 | Springer et al. |
| 4,787,591 A | 11/1988 | Villacorta |
| 4,840,391 A | 6/1989 | Schneider |
| 4,844,397 A | 7/1989 | Skakoon |
| 4,945,592 A | 8/1990 | Sims |
| 5,009,442 A | 4/1991 | Schneider |
| 5,169,106 A | 12/1992 | Rasmussen |
| 5,230,496 A | 7/1993 | Shillington |
| 5,355,539 A | 10/1994 | Boettger |
| 5,421,548 A | 6/1995 | Bennett |
| 5,499,721 A | 3/1996 | Hansen et al. |
| 5,588,166 A | 12/1996 | Burnett |
| 5,634,619 A | 6/1997 | Alessi |
| 5,704,526 A | 1/1998 | Kuo |
| 5,735,499 A | 4/1998 | Phillips et al. |
| 5,779,207 A | 7/1998 | Danby |
| 5,829,723 A | 11/1998 | Brunner |
| 6,425,561 B2 | 7/2002 | Wooten et al. |
| 6,450,462 B1 | 9/2002 | Hsieh |
| 6,622,980 B2 | 9/2003 | Boucher |
| 6,913,234 B2 | 7/2005 | Weiss |

*Primary Examiner* — Amy J Sterling
(74) *Attorney, Agent, or Firm* — Mark J. Nahnsen; Barnes & Thornburg LLP

(57) ABSTRACT

A clamping device for attaching a piece of first moveable equipment to a piece of second moveable equipment comprising a body, a mounting portion, and an attachment portion. The attachment portion comprising an attachment recess disposed within the body for receiving the piece of first movable equipment, and a latch plate rotatably attached to the body at a pivot disposed on one side of said attachment recess, wherein the latch plate may be pivotally disposed between an open position and a closed position. The latch plate further having an attachment lock disposed within the latch plate. The attachment lock is configured to produce a force against the piece of first moveable equipment when the latch plate is in the closed position.

3 Claims, 13 Drawing Sheets

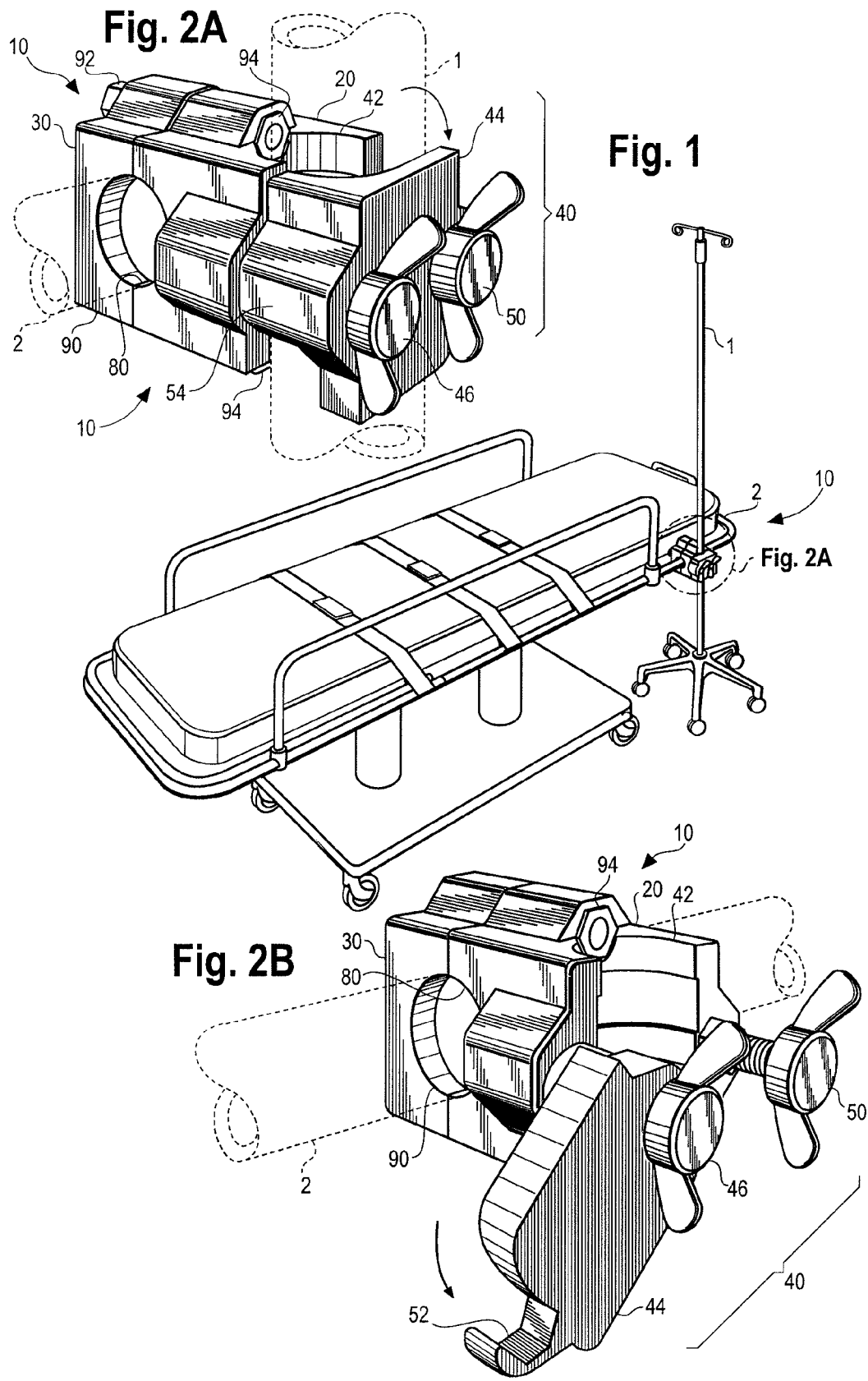

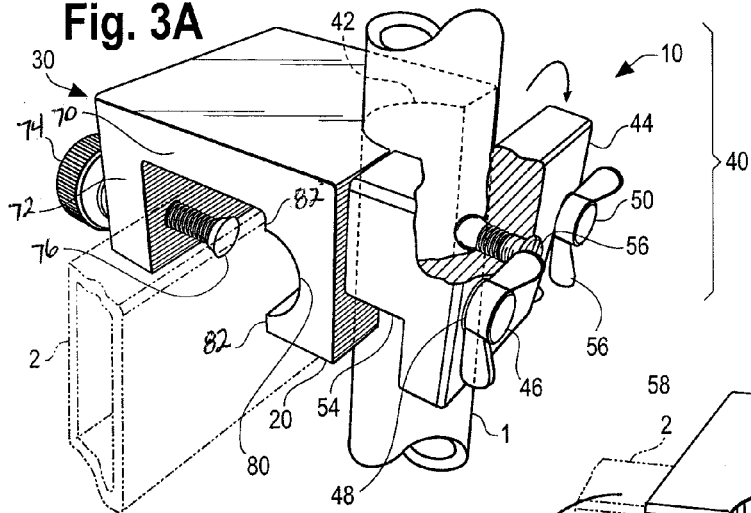
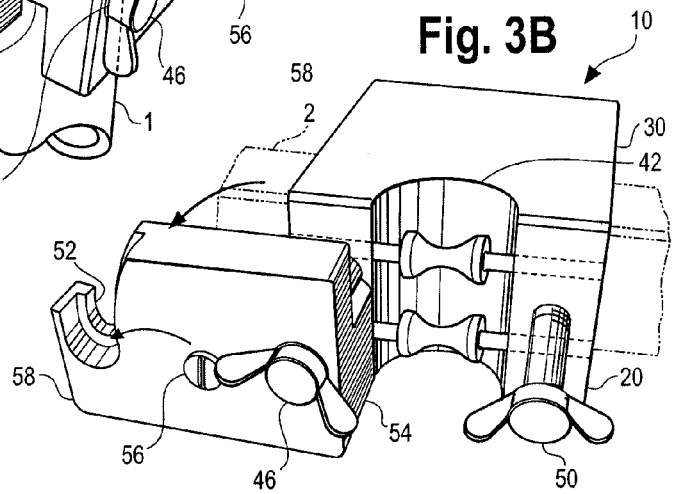
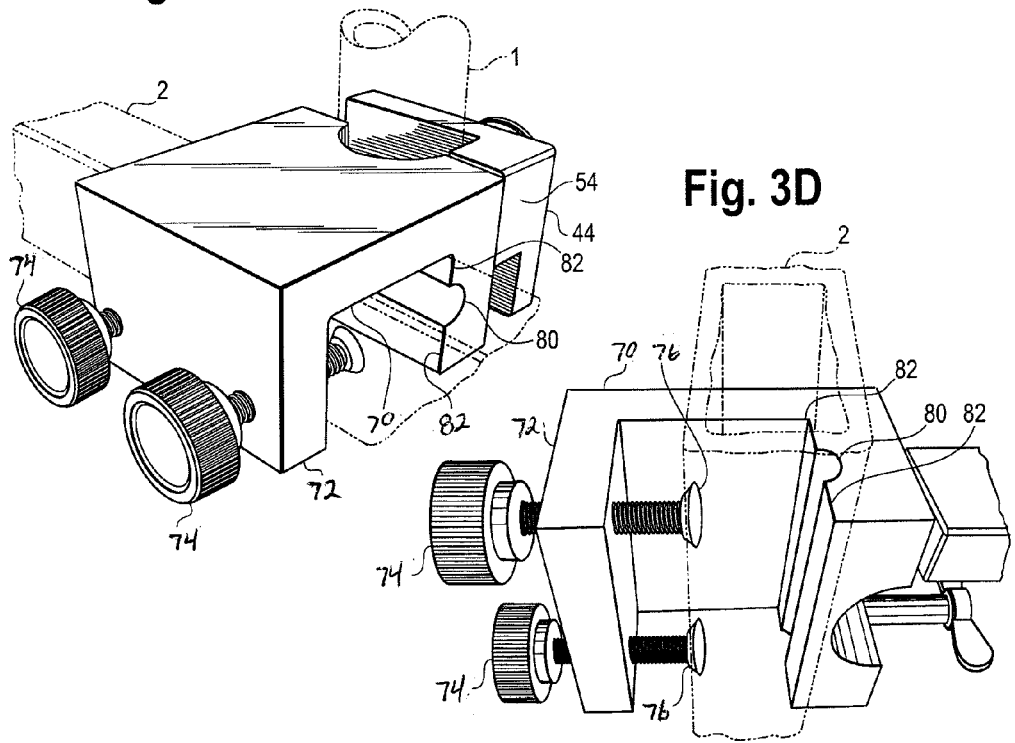

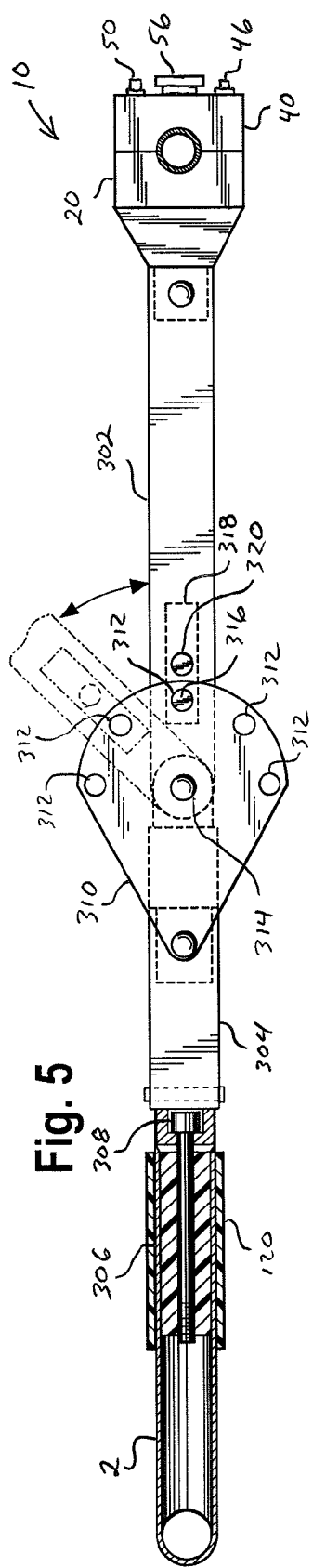
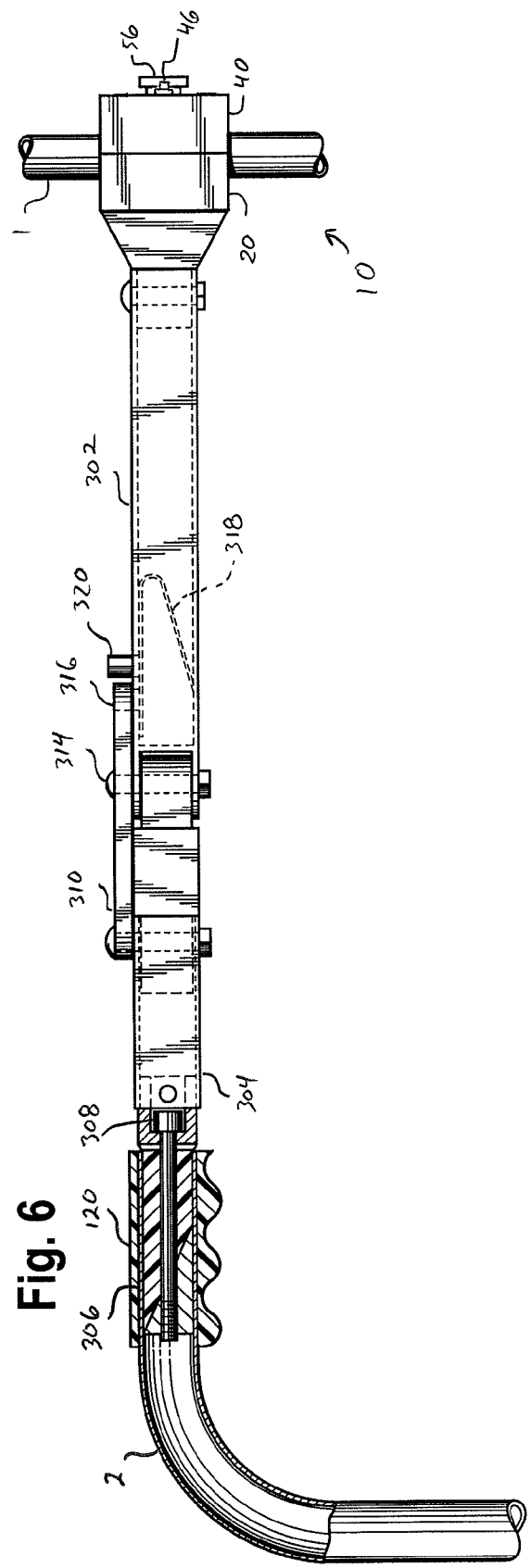
Fig. 5
Fig. 6

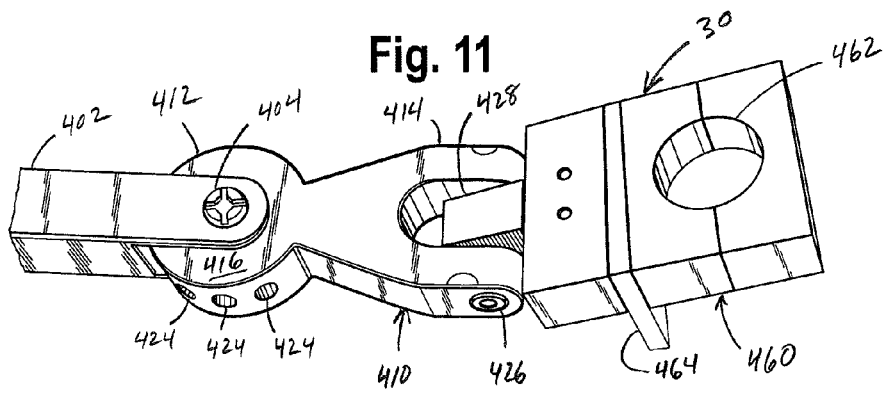
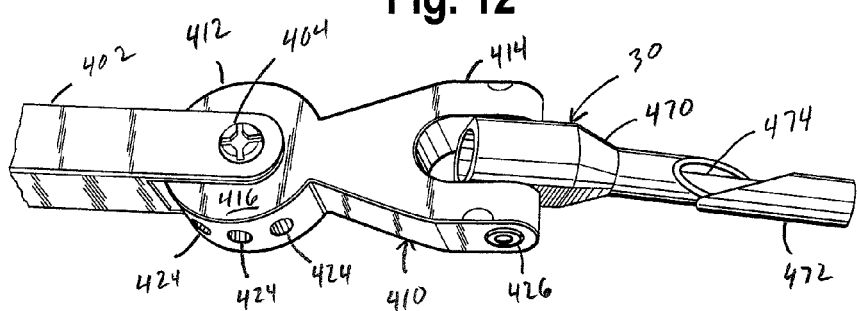
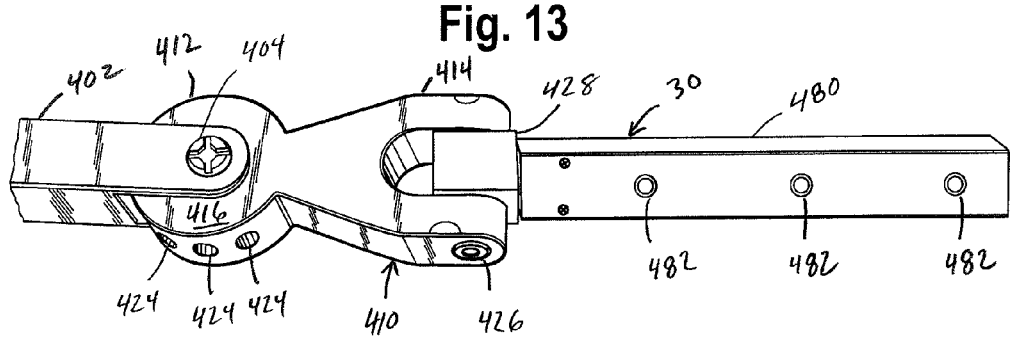

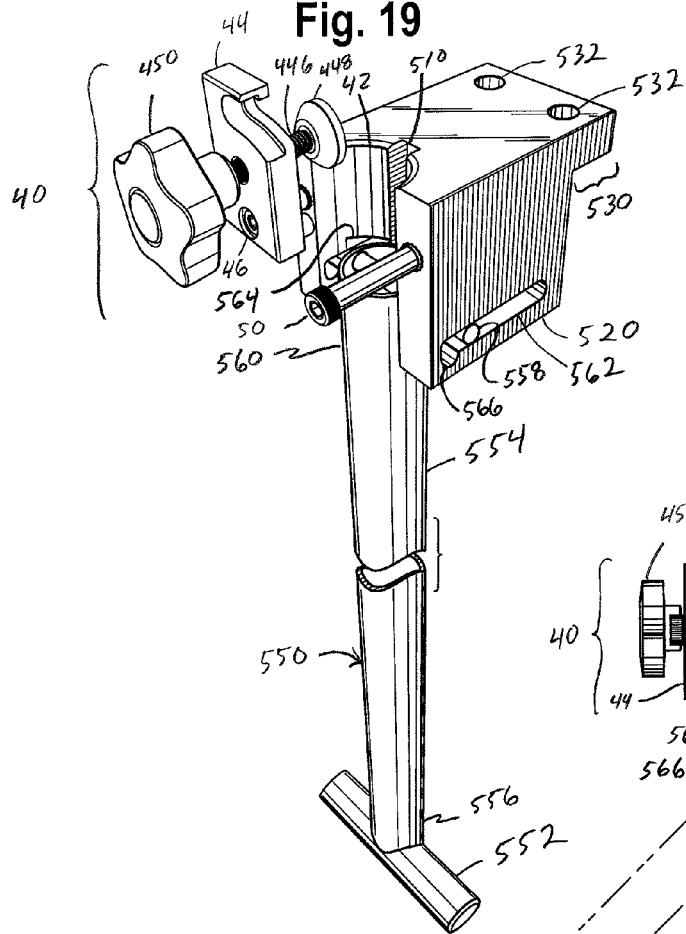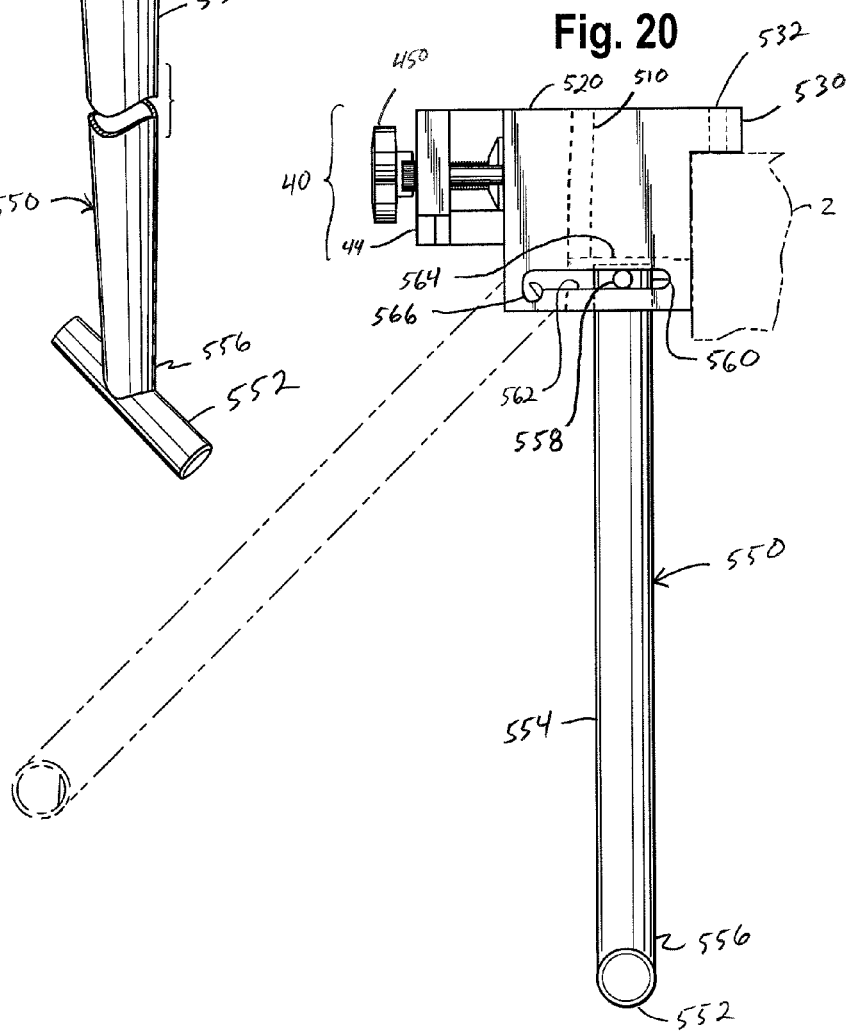

CLAMPING DEVICE

CROSS REFERENCE TO RELATED APPLICATIONS

The present application is a continuation-in-part of U.S. patent application Ser. No. 11/419,248, which is currently pending.

BACKGROUND

The present disclosure generally relates to a clamping device for quickly and removably joining two pieces of moveable equipment. In particular, the present disclosure is for a clamping device for attaching a first piece of moveable medical equipment such as an IV pole to a second piece of moveable medical equipment such as a hospital bed, gurney, stretcher, wheelchair, or other patient transport device.

In a hospital or other healthcare setting, it is common for a patient to undergo treatment that includes the administration of fluids and/or drugs intravenously. Such intravenous (IV) treatment generally requires a fluid or drug to be administered supplied in a bag or other container, be positioned at some height above the point of administration and the fluid be allowed to drip, by gravity, through tubing and into the patient's vein at an administration site. It is common to hang the bag or other container with the fluid from a pole (IV pole) during administration to alleviate the need for medical personnel to hold the container of fluid.

Such IV poles are well known in the art, and generally consist of a length of adjustable tubing having one or more hooks at the upper end for hanging the container of fluid and a base with a plurality of wheels or casters to allow the IV pole to be rolled along the floor.

It is also common for a patient undergoing IV treatment to be moved about a hospital or other medical facility to undergo other required procedures. For example, a patient undergoing IV treatment may need to be moved to surgery, to have X-rays taken, to have an MRI scan, to undergo radiation treatment, or to undergo another procedure. In moving the patient, the patient is usually transferred to a patient transport device such as a stretcher or wheelchair. A common practice is simply for someone to push the IV pole as the patient is being transported. However, for one person moving multiple items, such as a patient in a stretcher or wheelchair and an IV pole, at the same time can be awkward and can result in injury for the person moving the patient. For example, the IV tubing may become tangled and pulled from the patient, or the person transporting the patient may be injured trying to control a wheelchair or stretcher and an IV pole simultaneously.

A need exists to provide a device that allows an IV pole to be quickly and securely attached and detached to a patient transport device, while allowing the person transporting the patient to focus on control of the transport device.

Furthermore, many patient transport devices, such as stretchers, have a height adjustment feature that allow the transport device to be raised or lowered to match the surface on which a patient is supported. For example, a stretcher may be raised or lowered to match the height of a bed, table, or other support surface occupied by a patient. Therefore, there is also a need for an attachment device that moves along an IV pole that is supported on the floor while the transport device to which it is attached is raised or lowered, without binding on the IV pole and without causing the IV pole to rotate, twist, tilt, or otherwise become misaligned.

SUMMARY

The present disclosure is for a clamping device for attaching an IV pole to a piece of moveable medical equipment such as a bed, stretcher, wheelchair, or the like. The device of the present disclosure has a clamping portion for quickly receiving and securing an IV pole or similar structure, and a mounting portion for attachment to a piece of moveable medical equipment.

One aspect of the present disclosure includes a clamping device for attaching a piece of first moveable equipment to a piece of second moveable equipment comprising a body, a mounting portion, and an attachment portion. The attachment portion comprising an attachment recess disposed within the body for receiving the piece of first movable equipment, and a latch plate rotatably attached to the body at a pivot disposed on one side of said attachment recess, wherein said latch plate may be pivotally disposed between an open position and a closed position. The latch plate having a notch configured to cooperate with a latch pin when the latch plate is disposed in the closed position. The latch pin is attached to the body on one side of the attachment recess opposite the pivot. The latch plate may have a groove disposed on an edge thereof proximate to said pivot, wherein the groove is configured to cooperate with a stop attached to the body when the latch plate is in the open position. The latch plate may additionally have an attachment lock disposed within the latch plate. The attachment lock is configured to produce a force against the piece of first moveable equipment when the latch plate is in the closed position.

Another aspect of the present disclosure includes a mounting feature allowing the clamping device to be mounted to a structural member having either a rectangular or cylindrical configuration. This aspect of the disclosure includes a clamping device for attaching a piece of first moveable equipment to a piece of second moveable equipment comprising a body, a mounting portion, and an attachment portion. The mounting portion includes channel defined by a web extending from said body and a flange extending from said web. The mounting portion additionally has a mounting recess disposed on a face of the body within said channel. The mounting recess defines a first flat portion and a second flat portion positioned on either side of the mounting recess. The mounting portion may also have adjustable fasteners disposed through the flange, wherein the channel is configured to receive a portion of the second movable equipment with the fasteners securing the clamping device. The attachment portion has an attachment recess disposed within said body for receiving the piece of first movable equipment. A plurality of rollers may be disposed within the attachment recess. At least one of the plurality of rollers is positioned proximate to one end of said attachment recess and another of the plurality of rollers is positioned proximate to a second end of the attachment recess. The attachment recess defines a centerline and the rollers are mounted such that each has an axis of rotation substantially perpendicular to the centerline. The attachment portion also has a latch plate rotatably attached to the body at a pivot disposed on one side of the attachment recess, wherein the latch plate may be pivotally disposed between an open position and a closed position. The latch plate may have a notch configured to cooperate with a latch pin when the latch plate is disposed in the closed position. The latch pin is attached to the body on a side of the attachment recess opposite the pivot. The latch plate further may have a groove disposed on an edge thereof proximate to the pivot, wherein the groove is configured to cooperate with a stop attached to the body when the latch plate is in the open position. Additionally, the latch plate may further have a spring loaded ball bearing disposed within the latch plate. The spring loaded ball bearing is configured to produce a force against the piece of first moveable equipment when the latch plate is in the closed position.

Yet another aspect of the present disclosure includes a mounting feature for engagement with a handle of a wheelchair. This aspect of the disclosure includes an insert to engage the inside surface of a tubular wheelchair handle, and an extension portion pivotally coupled to the insert. A pivot plate is fixed to the insert having a plurality of apertures for engagement with a depressible pin mounted in the extension. The pin is attached to a spring within the extension. A button is provided for a user to depress the spring to disengage the pin from the pivot plate, allowing the extension to be pivoted to a desired orientation. The user may then release the button to engage the pin within an aperture to secure the extension.

BRIEF DESCRIPTION OF THE DRAWINGS

FIG. 1 is a perspective view showing an embodiment of the present disclosure attaching an IV pole to a stretcher;

FIG. 2A is a perspective view showing an embodiment of the present disclosure with an attachment portion in the closed position;

FIG. 2B is a perspective view showing the embodiment of FIG. 2A with an attachment portion in the open position;

FIG. 3A is a cut-away perspective view of another embodiment of the present disclosure having a locking mechanism in the attachment portion holding the IV pole in place, and the mounting portion configured for rectangular structural members;

FIG. 3B is a front perspective view of the embodiment of FIG. 3A, showing the attachment portion in the open position;

FIG. 3C is a rear perspective view of the embodiment of FIG. 3A;

FIG. 3D is a bottom perspective view of the embodiment of FIG. 3A;

FIG. 5 is a top view of another embodiment of the present disclosure with the mounting portion adapted to engage a handle of a wheelchair;

FIG. 6 is a side view of the embodiment of FIG. 5;

FIG. 11 is a perspective view of another embodiment of the mounting portion of the device of FIG. 9;

FIG. 12 is a perspective view of another embodiment of the mounting portion of the device of FIG. 9;

FIG. 13 is a perspective view of another embodiment of the mounting portion of the device of FIG. 9;

FIGS. 18A and 18B are perspective views of an embodiment of an attachment portion of the device of the present disclosure, wherein FIG. 18A is in a closed position, and FIG. 18B is in an open position;

FIG. 19 is a perspective view of another embodiment of the clamping device of the present disclosure;

FIG. 20 is a side view of the embodiment of FIG. 19; and

DETAILED DESCRIPTION

Referring to FIG. 1, a clamping device 10 is provided to attach a first piece of moveable equipment such as an IV pole 1 to a structural member 2 of a second piece of moveable equipment such as a patient transport device. Specifically, FIG. 1 shows a stretcher, however it should be clear to one skilled in the art that the clamping device of the present disclosure may be used with beds, wheelchairs, and other moveable equipment used to transport patients that are undergoing IV fluid treatment.

Figure 4A:
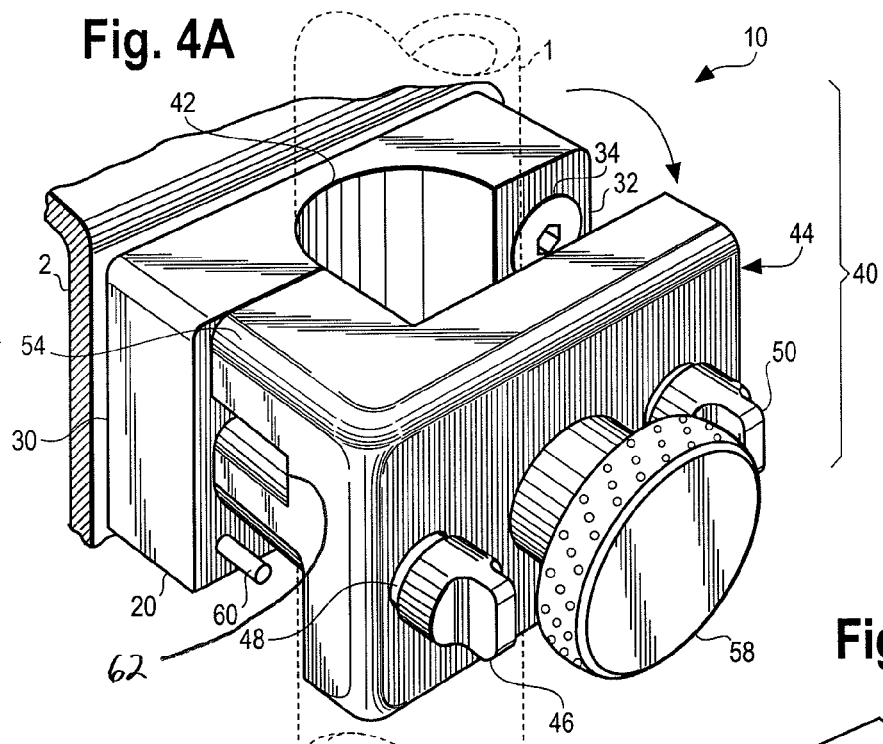
FIG. 4A is a perspective view of another embodiment of the present disclosure having an alternative mounting means.
Figure 4B:
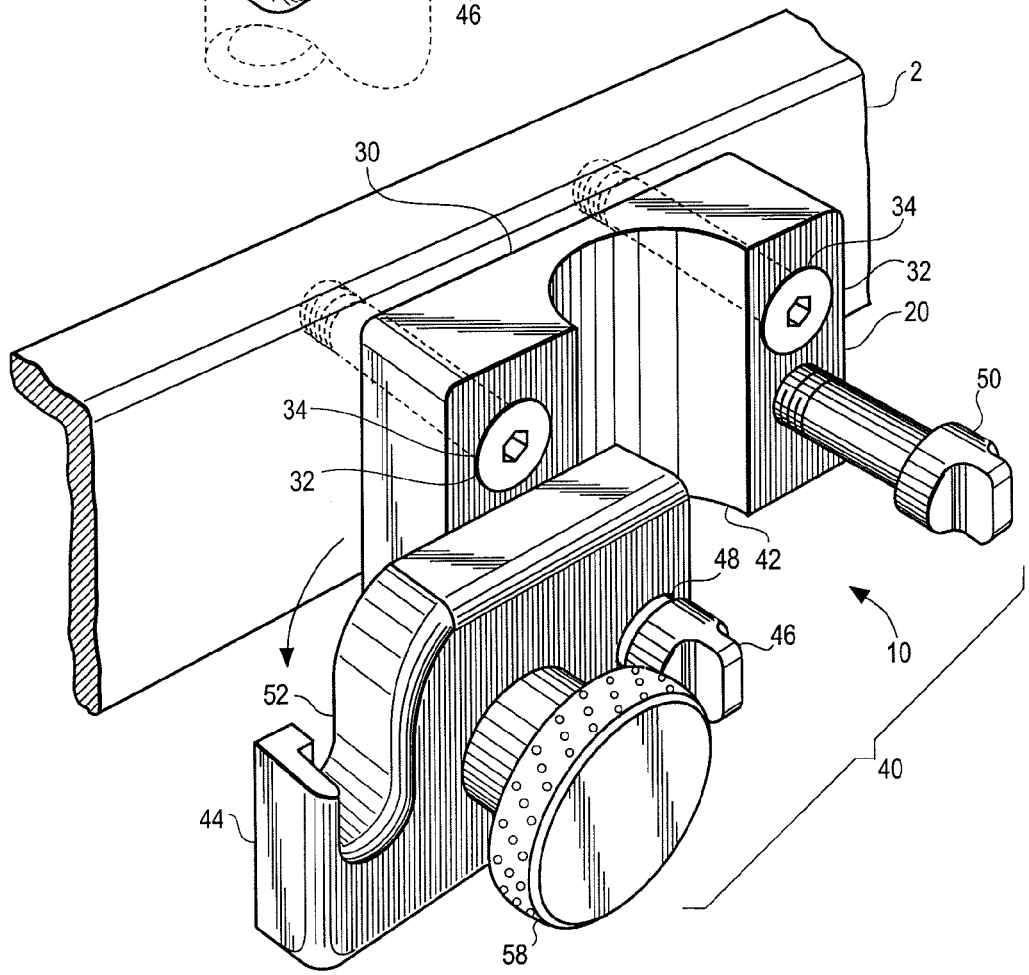
FIG. 4B is a perspective view of the embodiment of FIG. 4A showing the attachment portion in the open position.
Figure 7:
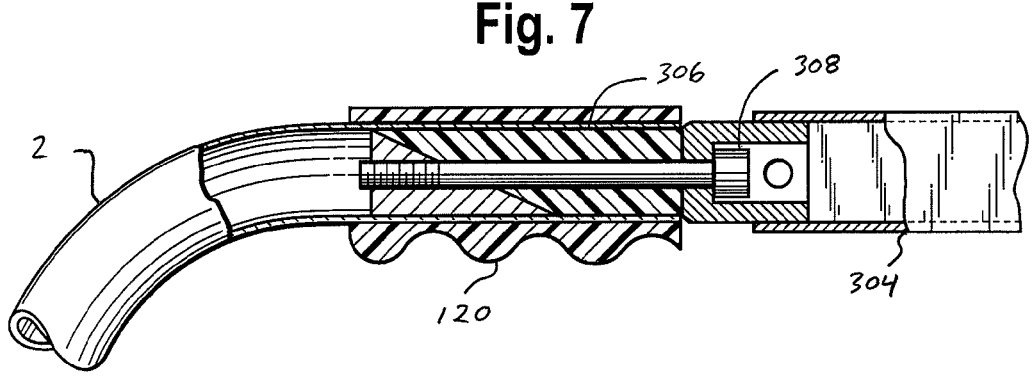
FIG. 7 is a detailed view of showing the mounting portion of the embodiment of FIG. 5.
Figure 8:
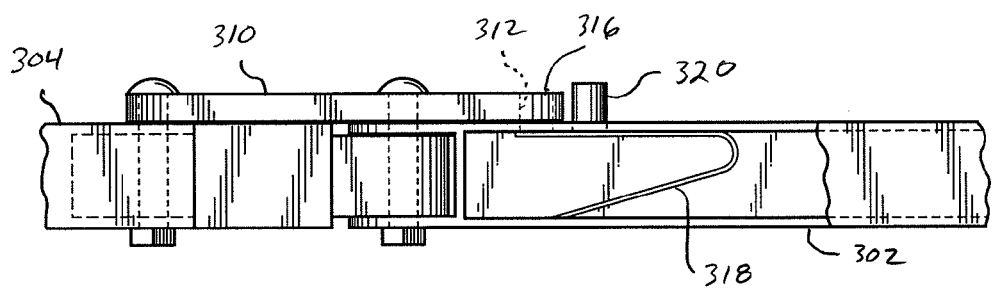
FIG. 8 is a cut-away view showing the adjustment pin arrangement of the embodiment of FIG. 5.
Figure 9:
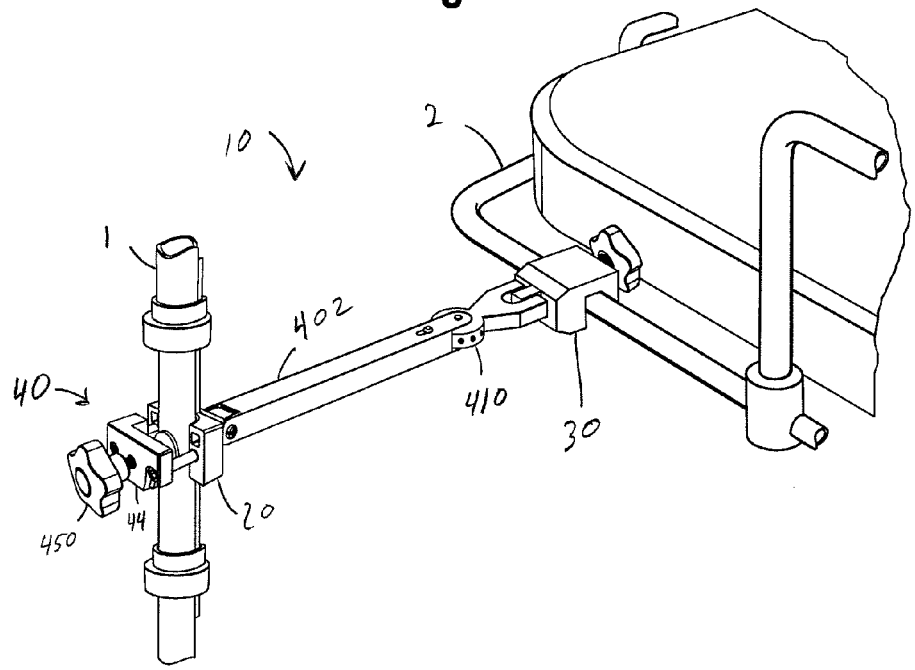
FIG. 9 is a perspective view of another embodiment of the present disclosure including an extension pivotally coupled to a mounting portion and pivotally coupled to an attachment portion.

Referring to the embodiment shown in FIGS. 4A and 4B, the clamping device of the present disclosure has body 20 with a mounting portion 30 and an attachment portion 40. The mounting portion 30 is configured to be positioned on a piece of moveable medical equipment 2. The mounting portion 30 of the embodiment shown in FIGS. 4A and 4B is configured to cooperate with a relatively flat structural member such as a piece of rectangular tubular channel or the like. Mounting portion 30 comprises a mounting face 36 for cooperation with a flat face of a structural member of medical equipment 2. Fasteners 32 are disposed within apertures 34 extending through the body 20, securing the clamping device 10 to the medical equipment 2. Although the fasteners 32 shown in FIGS. 4A and 4B are shown as allen head set screws, it should be apparent to one skilled in the art that other fasteners such as counter sunk screws, bolts, rivets, and the like are equally acceptable.

Opposite the mounting portion 30 is an attachment portion 40. The attachment portion 40 has an attachment recess 42 and a latch plate 44. The latch plate 44 is pivotally attached to the body 20 at one side of the attachment recess 42. Latch plate 44 is pivotally attached such that in a first position, as shown in FIG. 4A, the latch plate 44 is positioned to close off access to attachment recess 42, while in a second position, as shown in FIG. 4B, the latch plate 44 is pivoted out of the way, allowing access to the attachment recess 42.

The latch plate 44 is connected to the body by a pivot 46 disposed within an aperture 48 extending through the latch plate at one side thereof. A latch pin 50 is provided on the body 20 on the opposite side of the attachment recess 42 as pivot 46. The latch pin shown in FIG. 4B is a thumb screw threadedly connected to the body 20. Although a thumbscrew is shown, it should be apparent that other embodiments are possible such as a threaded rod with a wing nut, or a straight post. A notch 52 is provided in the latch plate 44 and is configured to receive latch pin 50 when the latch plate 44 is in the closed position.

In the embodiment shown in FIGS. 4A and 4B, the latch plate 44 is configured as a generally rectangular plate having a projection 54 at an upper corner adjacent pivot 46. Projection 54 operates to space the latch plate 44 a predetermined distance from the body 20 to allow for placement of IV pole 1 in recess 42. Projection 54 is configured such that one side of IV pole 1 is received into recess 42 while sufficient clearance is provided to allow the latch plate 44 to pivot freely into the closed position wherein the latch pin 50 is received into notch 52.

In the embodiment presented in FIGS. 4A and 4B, the latch pin 50 takes the form of a thumb screw to tighten against the latch plate 44 and maintain the latch plate in the closed position. Another feature is an attachment lock 56 disposed within the latch plate 44. The attachment lock 56 locks the IV pole 1 in place within the attachment recess 42 of the clamping device 10. The attachment lock provides a generally horizontal force directed towards the attachment recess 42, forcing the IV pole 1 into the recess.

In the embodiment of FIGS. 4A and 4B, a knob 58 or other gripping feature may be provided to easily adjust the attachment lock 56. Using the knob 58, the attachment lock 56, being a threaded rod, may be adjusted by turning the threads so that the rod is driven to engage IV pole 1 and provide a positive force securing the IV pole in place.

An alternate embodiment for the attachment lock 56 is shown in FIGS. 3A and 3B comprising a spring loaded ball bearing 110 to supply the horizontal force against the IV pole 1. In this embodiment, the latch plate 44 has a well 114 disposed within the side facing the attachment recess 42. Within the well is a spring 112 and a ball bearing 110. The well lip 116 is sized to be slightly smaller than the diameter of ball bearing 110 to retain the ball bearing within the well 114. The latch plate 44, and the spring-loaded ball bearing 110 are configured such that when an IV pole is disposed within the attachment recess 42 and latch plate 44 is in the closed position, IV pole is in contact with ball bearing 110 tending to push the ball bearing 110 into the well 114. The spring 114 provides a force against the IV pole 1, engaging the IV pole with the attachment recess 42, locking the IV pole in place. In yet another embodiment (not shown), the attachment lock may comprise a roller or a spring loaded roller on the inner surface of latch plate 44.

A stop 60 is provided on the body 20 to limit rotation of the latch plate 44. The stop 60 is positioned on the body 20 to be received within a groove 62 on the latch plate 44. As the latch plate 44 is rotated into the open position, the stop 60 is received into groove 62 and prevents further rotation when the attachment portion 40 is in the fully open position. This feature prevents interference between the IV pole 1 and the latch plate 44 when positioning the IV pole 1 within the attachment recess 42. Generally, it is preferred to configure the stop 60 and groove 62 such that rotation of the latch plate 44 is limited to 180 degrees or less. However, one skilled in the art should easily understand that the latch plate 44 may have different configurations that provide clear access to the attachment recess 42 when in the open position.

Another embodiment of the clamping device is shown in FIGS. 3A through 3D. In this embodiment, the mounting portion 30 is configured to be releasably attachable to a structural element of a patient transport device 2. The mounting portion 30 of this embodiment is generally configured as a channel having a web 70 and flange 72. The rear portion of the body 20, along with the web 70 and flange 72 define a channel configured to receive structural member 2. One or more set screws 74 are provided to secure the clamping device 10 to the structural member 2. The set screw 74 may also include pads 76 for contact with structural member 2 to prevent scratching and marring.

The rear side of body 20 may also include a mounting recess 80 disposed between two flats 82. In the embodiment shown, the mounting recess 80 has a concave arcuate profile. This configuration allows the clamping device 10 to be attached to either rectangular or cylindrical structural members 2. In the case of a rectangular structural member, the flats 82 engage one side of the structural member while the set screws 74 secure the opposite side. In the case of a cylindrical structural member, the arcuate mounting recess 80 receives and engages the cylindrical member while the set screws secure the opposite side. This feature eliminates the need for different clamping devices to accommodate different shaped structural members.

Referring now to yet another embodiment of the present disclosure shown in FIGS. 2A and 2B, a clamping device 10 may be configured for more permanent attachment to a structural member 2. Although still removably attached to a structural member 2, the embodiment of the clamping device 10 shown in FIGS. 2A and 2B requires tools to remove the clamping device from the structural member.

In this particular embodiment, the mounting portion 30 is connected the body 20 so as to have the clamping device 10 disposed about structural member 2. The rear side of the body 20 has a mounting recess 80 similar to that described above. Mounting portion 30 has a corresponding second mounting recess 90 that is configured to mirror mounting recess 80. The body 20 and the mounting portion 30 are connected by releasable fasteners. The drawings show a hex-head bolt 92 and hex nut 94, although it should be clear to one skilled in the art that other types of releasable fasteners such as screws, pins, etc. are equally acceptable.

Although not shown, the mounting recess 80, and second mounting recess 90 may also be configured with straight sides, rather than an arcuate profile, creating a rectangular channel for connection to a rectangular structural member.

Referring now to FIG. 3B, another feature that may be incorporated into the device and still be within the scope of the present disclosure includes one or more tapered rollers 100 within the attachment recess 42. The rollers 100 having a concave or "bow-tie" profile adapted to fit the cylindrical contour of an IV pole 1. Each roller 100 is positioned on a shaft 102 such that the roller is configured having a substantially horizontal axis of rotation.

For example, one common application of the device of the present disclosure, is for attaching an IV pole 1 to a structural member 2 of a stretcher used to transport patients. Such stretchers as are commonly known in the art are equipped with either manual or hydraulic lifts to adjust the height of the stretcher. Often a patient undergoes treatment requiring multiple IV fluids that are attached to the pole 1. The tubing for administering the IV fluids may become tangled, or worse, be inadvertently pulled out of the patient should the IV pole 1 rotate. Therefore, it is desirable to maintain the orientation of the IV pole 1 relative to structural member 2, especially if structural member 2 is being raised or lowered.

The rollers 100 used in conjunction with a spring-loaded ball bearing 110 as the attachment lock allow the clamping device 10 to roll along the surface of the IV pole 1 as the stretcher is raised and lowered without binding upon the IV pole 1. The tapered rollers 100 are configured to roll along an arcuate portion of the IV pole 1 while the spring-loaded ball bearing 110 rolls along the opposite side while pushing the IV pole 1 towards the rollers 110. This configuration allows for smooth movement between the clamping device 10 and the IV pole 1, greatly reducing the tendency to bind, which may cause the IV pole 1 to rotate, twist, or tilt.

Referring now to FIGS. 5 through 8, another embodiment of the present clamping device 10 has a mounting portion 30 configured for mounting on a piece of moveable medical equipment 2 comprising a wheelchair. In this embodiment, the body 20 and attachment portion 40 are as previously described. The mounting portion 30 is configured to attach to the handle of a wheelchair.

A typical wheelchair has a pair of hand grips mounted on the rear of the chair enabling a person to push the chair. In attaching an IV pole 1 to a wheelchair, care must be taken to avoid interference with the wheels and with the person pushing the wheelchair. The mounting portion 30 has an extension 302 attached to the body 20 opposite the attachment portion. The extension 302 is pivotally connected to an insert 304 that is inserted into the tubular portion of a wheelchair hand grip 120. In the embodiment shown, insert 304 is secured within the hand grip 120 by a cylindrical wedge 306 and thumb screw 308. The cylindrical wedge 306 is inserted into the hand grip 120 of the wheelchair and tightened against the inside surface of the hand grip by the thumbscrew 308.

A pivot plate 310 is fixed to the insert 304 opposite the cylindrical wedge 306. The pivot plate has a plurality of apertures 312 arranged about the extension pivot 314. The apertures 312 are configured to receive a pin 316 attached to the extension 302. Within extension 302 is a spring 318 having the pin 316 attached. A button 320 is provided to depress the spring 318 and thus the pin 316, disengaging the pin from one of the apertures 312 in the pivot plate 310. With the pin 316 disengaged from the pivot plate 310, the extension 302 is freely pivotable about extension pivot 314. The extension 302 may then be positioned so that the pin 316 engages one of the apertures 312 by releasing button 320. This allows the clamping device 10 at the end of extension 302 to be positioned at various locations behind and to the side of the wheelchair.

Figure 14:
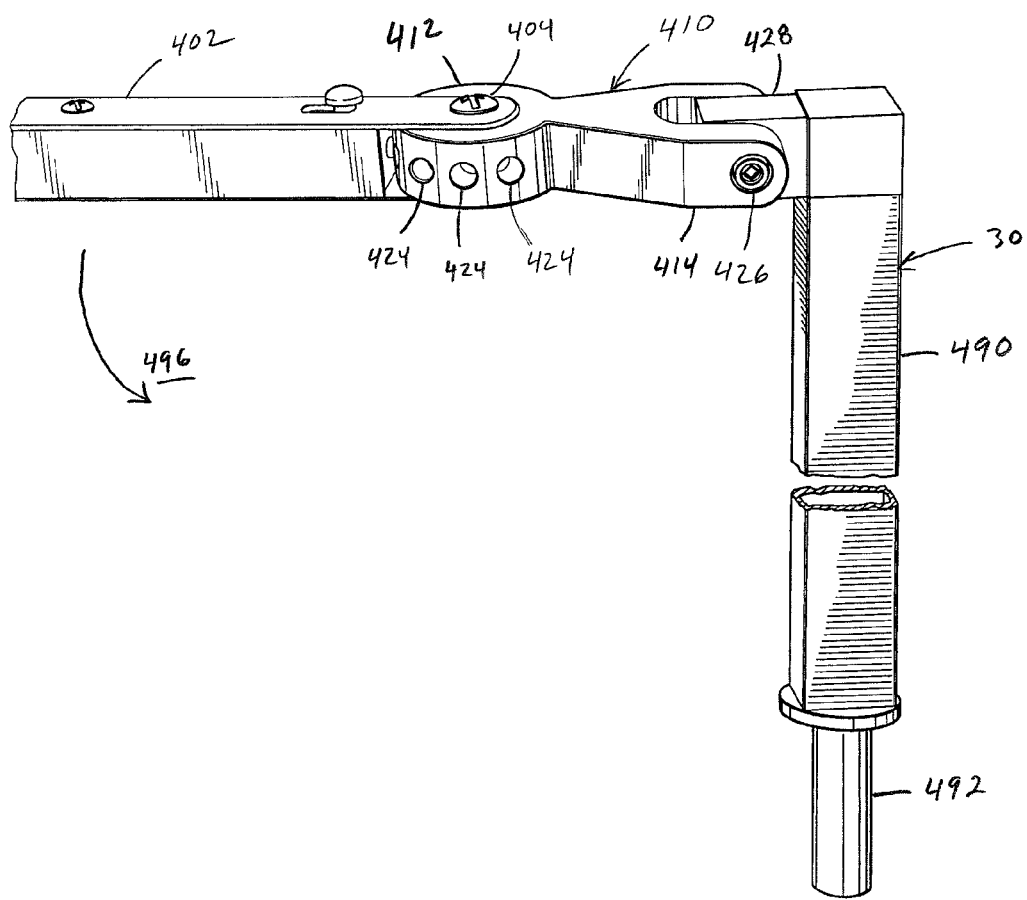
FIG. 14 is a perspective view of another embodiment of the mounting portion of the device of FIG. 9.
Figure 15:
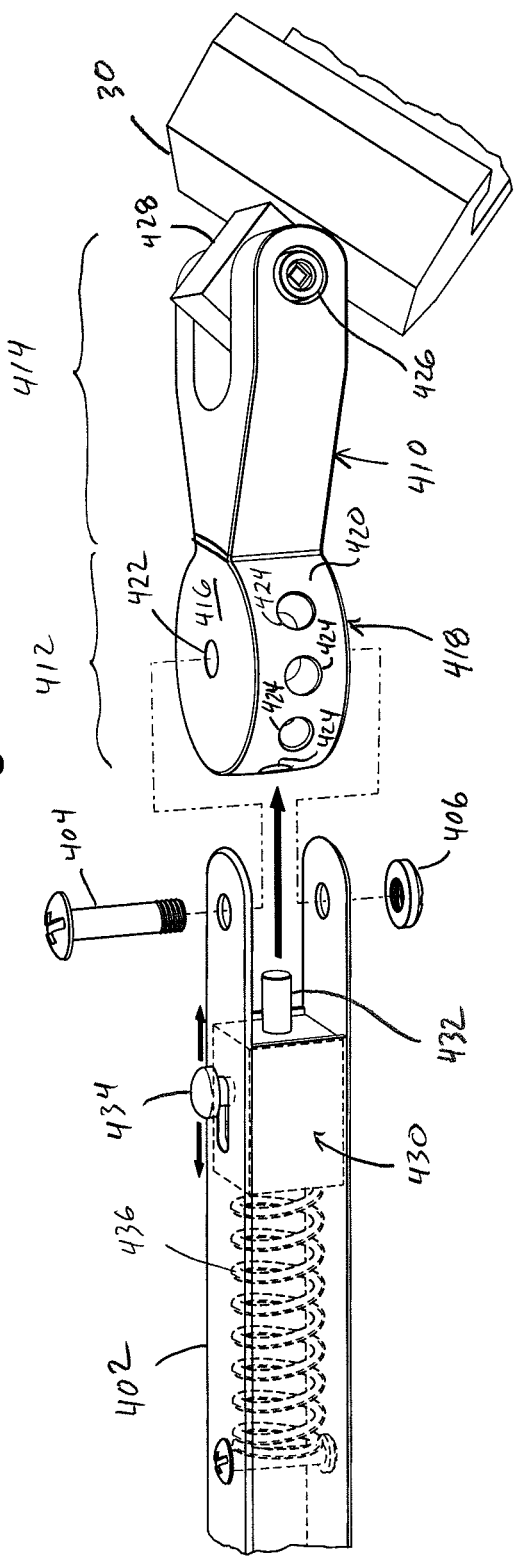
FIG. 15 is an exploded perspective view of extension pivot assembly of the embodiment of FIGS. 9-14.

Another embodiment of the clamping device 10 of the present disclosure shown in FIGS. 9-18B and FIG. 21, includes a mounting portion 30, a body 20, an attachment portion 40, and an extension 402. A pivot assembly 410 is coupled to the extension 402. Referring to FIG. 15, pivot assembly includes a drum 412 and a yoke 414. The drum 412 includes a top 416, a bottom 418, and a arcuate sidewall 420. An aperture 422 is provided through the top 416 and bottom 418 of the drum for pivotal attachment to the extension 402. A fastener 404, such as a screw, bolt, threaded rod, or the like is disposed through aperture 422 and secured with a suitable retainer 406, such as a nut, retaining ring, cotter pin, or the like. Drum 412 further includes a plurality of radial apertures 424 disposed in the arcuate sidewall 420.

The yoke 414 includes an axle 426 configured to couple a pivot block 428 to the yoke 414 allowing rotation of the pivot block in a plane perpendicular to the axle 426. Pivot block 428 is also pivotally coupled to mounting portion 30 such that the pivot block 428 and the mounting portion 30 are allowed to rotate relative to each other in a plane substantially perpendicular to the plane of rotation of the pivot block 428 about axle 426.

Extension 402 includes a locking assembly 430 having a biased member 432 configured for engagement with the plurality of radial apertures 424 disposed in the arcuate sidewall 420 of the pivot assembly 410 drum 412. Biased member 432 is shown as a pin configured to extend into the plurality of apertures 424 thereby locking extension 402 relative to pivot assembly 410. A thumb knob 434 may be provided to retract biased member 432 against the biasing force provided by a biasing member 436, such as the spring shown in FIG. 15. A user may pull back thumb knob 434, retracting the biased member 432 to disengage it from the pivot assembly 410, change the position of the extension 402, and release the thumb knob 434 causing biased member 432 to engage an aperture 424 in the pivot assembly. Extension 402 in cooperation with pivot assembly 410 allows the IV pole 1 to be positioned in such a was so as to not interfere with a person pushing a piece of movable medical equipment 2 such as a stretcher or bed.

Figure 21:
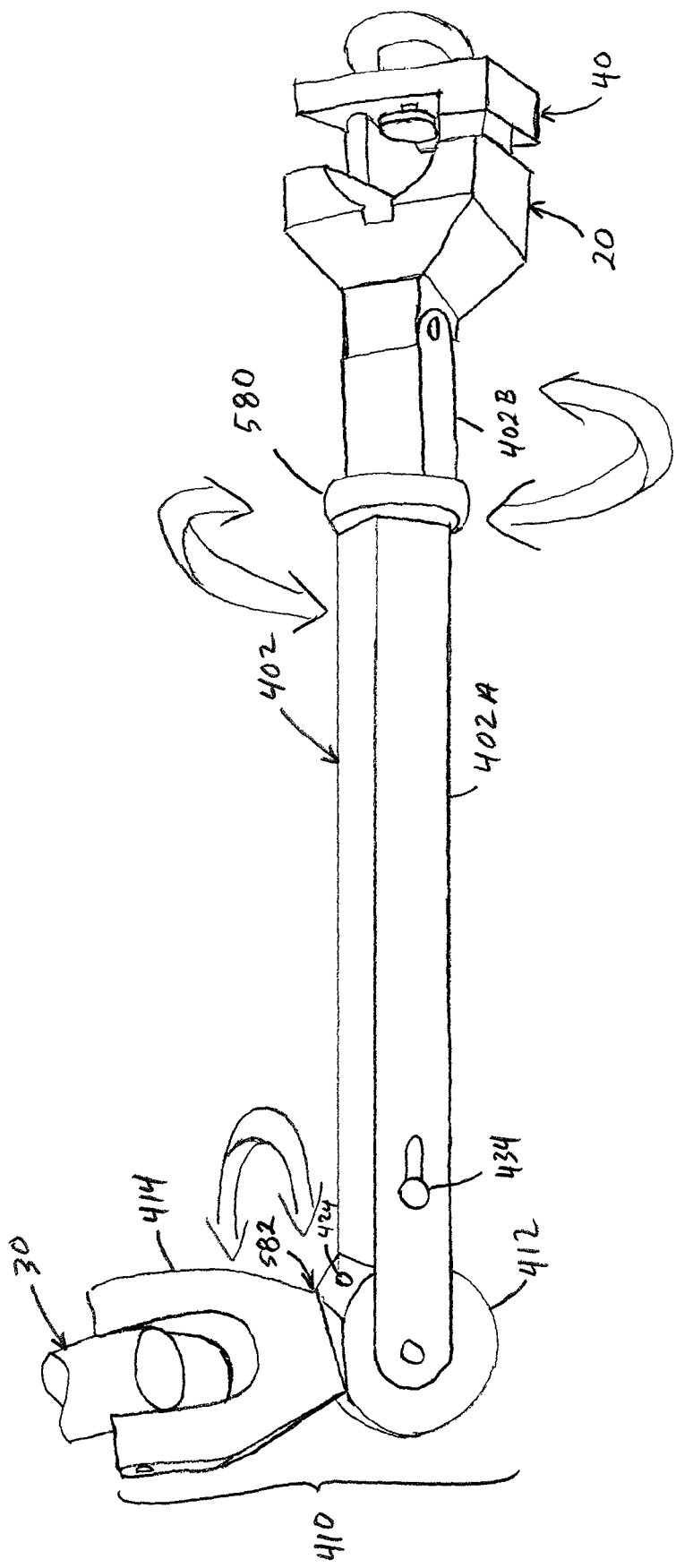
FIG. 21 is a perspective view of an alternative embodiment of the extension pivot assembly of the present disclosure.

Referring to FIG. 21, an alternate embodiment of extension 402 may include a swivel connector 580. Swivel connector 580 joins a first extension portion 402A with a second extension portion 402B such that first extension portion 402A and second extension portion 402B are permitted to rotate relative to each other about the long axis of extension 402. Further, a second swivel connector 582 may pivotally couple the drum 412 to the yoke 414 of the pivot assembly 410. Swivel connectors 580, 582 may be configured to allow full 360-degree rotation or may be configured to allow less than full rotation. Pivotally coupling the various members of extension 402 allows the present exemplary embodiment of the clamping device 10 of the present disclosure to compensate for uneven floor surfaces so at to mitigate the possibility of IV pole 1 tipping during transit. Pivotally coupling of 402A and 402B further allows for changes in elevation of a piece of movable medical equipment, such as when a stretcher is tilted, for example, with the head end downward into the Trendelenburg position.

Figure 10:
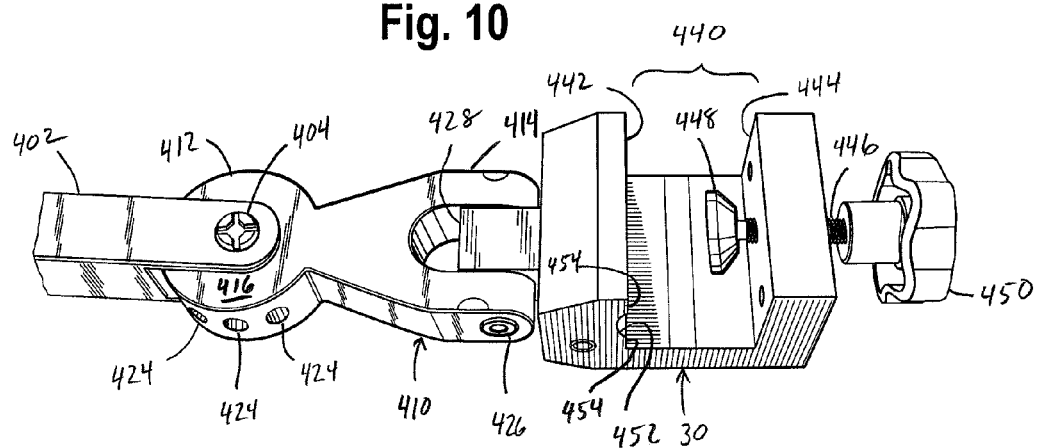
FIG. 10 is a perspective view of an embodiment of the mounting portion of the device of FIG. 9.

Referring now to FIG. 10, extension 402 is pivotally coupled to pivot assembly 410 by fastener 404. Pivot assembly 410 includes a pivot block 428 configured for rotation about axle 426. Pivot block 428 is also pivotably coupled to mounting portion 30. In the embodiment of FIG. 10, mounting portion 30 is configured for removable attachment to the frame of a movable piece of medical equipment such as a bed, gurney, wheelchair, and the like. Mounting portion 30 includes a channel 440 defined by a web 442 and a flange 444. Channel 440 is configured to receive a structural member. A set screw 446 is provided to secure mounting portion 30 to the structural member. Set screw 446 may further include a pad 448 to prevent scratching and marring. Set screw may also include a knob 450 to facilitate engagement and disengagement of the set screw without the use of tools.

Web 442 may also include a mounting recess 452 disposed between a pair of flats 454. In the exemplary embodiment of FIG. 10, the mounting recess 452 has a concave arcuate profile. This configuration allows the mounting portion 30 to be attached to a structural member having either rectangular or cylindrical shape. In the case of a rectangular structural member, the flats 454 engage one side of the structural member while the set screw 446 engages the opposite side. In the case of a cylindrical member, the arcuate mounting recess 452 receives and engages the cylindrical member while set screw 446 secures the opposite side. This feature eliminates the need for different clamping devices to accommodate different shaped structural members.

Referring to FIG. 11, another embodiment of the mounting portion 30 may be configured for mounting about a structural member of a piece of movable medical equipment. In this exemplary embodiment, mounting portion 30 is rotatably coupled to pivot block 428. Mounting portion 30 includes a body 460 defining an aperture 462. The aperture 462 may be of any appropriate shape corresponding to the structural member of the piece of second movable medical equipment. A guide plate 464 is provided and configured to engage the piece of movable medical equipment to prevent rotation of mounting portion 30 about the structural member.

Referring to FIG. 12, another embodiment of the mounting portion 30 may be configured for insertion into a tubular structural member of a piece of movable medical equipment, such as the handle of a wheelchair, as described above. As shown in FIG. 12, Mounting portion 30 is pivotally coupled to pivot assembly 410 about axle 426. Mounting portion 30 includes a body 470 and a cylindrical wedge 472. The cylindrical wedge is coupled to a shaft 474, which is rotatably coupled to the body 470. In this exemplary embodiment, mounting portion may be inserted into a tubular structural member, such as the handle of a wheelchair, and rotated to engage the cylindrical wedge 472 with the inner sidewall of the tubular structural member.

Referring to FIG. 13, another embodiment of mounting portion 30 may be configured for permanent and/or semi-permanent attachment within a tubular structural member of a movable piece of medical equipment. In the exemplary embodiment shown in FIG. 13, mounting portion 30 includes a member 480 configured to cooperate with the inner profile a tubular structural member. In the embodiment of FIG. 13, the member 480 is configured for insertion into a tubular structural member having a square or rectangular profile. The member 480 is rotatably coupled to pivot block 428 such that member 480 rotates about its longitudinal axis relative to pivot block 428. Member 480 may further include one or more mounting apertures 482. Mounting apertures are configured for cooperation with fasteners such as screws, bolts, rivets, and the like, requiring the use of tools for mounting and removal of mounting portion 30, thus providing permanent and/or semi-permanent mounting.

Referring to FIG. 14, another embodiment of mounting portion 30 may be configured to cooperate with a socket on a piece of movable medical equipment, such as a bed. In this exemplary embodiment, mounting portion includes a stanchion 490 having a socket pin 492 located at one end. The opposite end of stanchion 490 is rotatably coupled to pivot block 428. It is common for hospital beds to have a socket for mounting an IV pole directly to the bed frame. Socket pin 492 is configured to be inserted into such a socket on the frame of a hospital bed. Although it is common for hospital beds to have provisions for mounting an IV pole, it is also common for a portable IV pole to be regularly used. This embodiment of the present disclosure allows a patient to be moved in the bed without the need to transfer any of the IV fluids. When not in use, extension 402 and pivot assembly 410 may be folded down as shown by arrow 496 in FIG. 14 against stanchion 490 for compact storage. A retaining clip (not shown) may also be provided to secure extension 402 to stanchion 490 when not in use.

Figure 16:
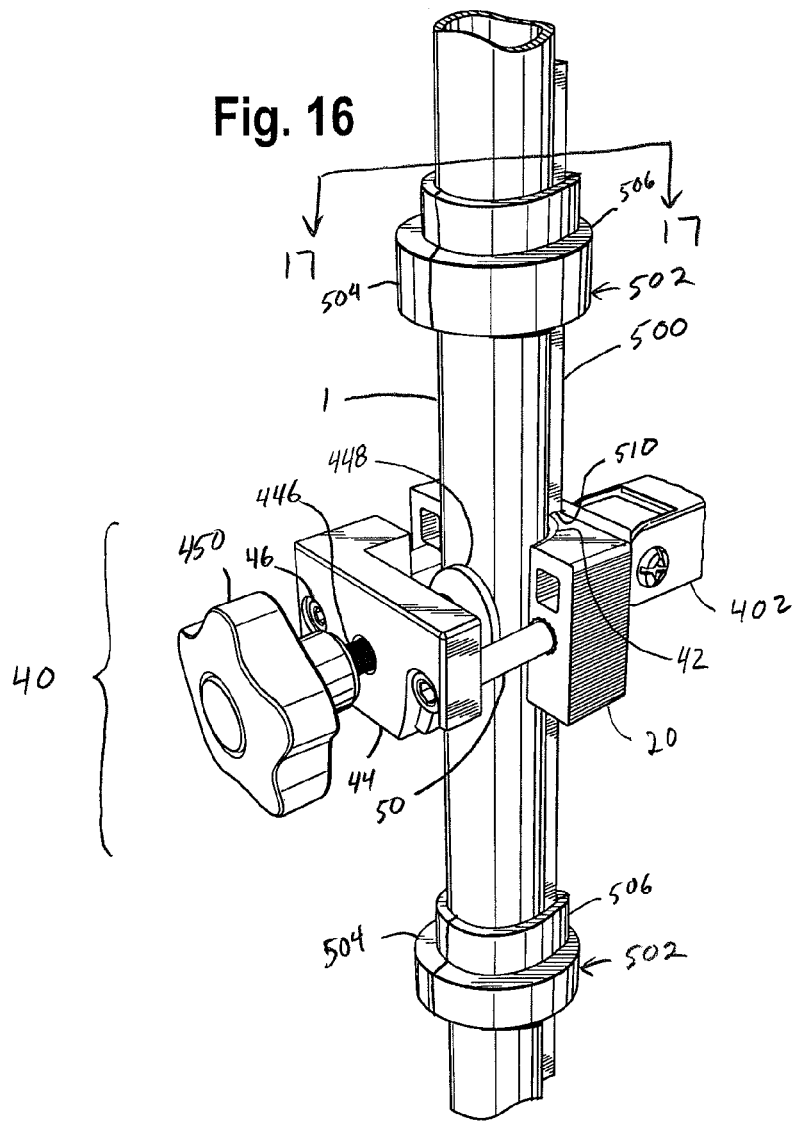
FIG. 16 is a perspective view of an embodiment of the attachment portion of the device of the present disclosure including an IV pole with removable anti-rotation key.
Figure 17:
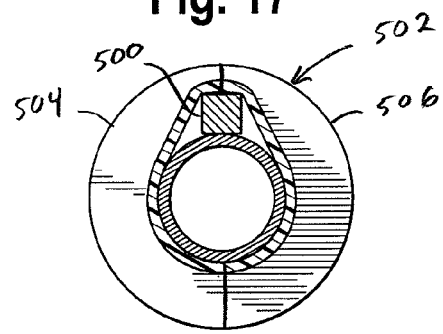
FIG. 17 is a section view taken at 17-17 of FIG. 16 showing the anti-rotation key attached to the IV pole.

Another aspect of the present disclosure includes an anti-rotation key 500 to prevent the IV pole 1 from rotating during transport which could result in tangling of intravenous fluid tubing, or worse, pulling the intravenous line out of the patient. It is common for most portable IV poles to consist of a pole 1 attached to a base with wheels and a hook or bail for hanging IV fluids. Therefore, a removable anti-rotation key 500 may be attached to IV pole 1 with one or more collars 502, as shown in FIG. 16. In the exemplary embodiment, the anti-rotation key 500 may be fabricated from steel key stock, aluminum, plastic, or other suitable material. As shown in FIG. 17, collar 502 includes cooperating mating portions 504, 506 configured for mounting about IV pole 2 and anti-rotation key 500. In the embodiment shown, mating portions 504 and 506 are configured to engage each by snap locking in place. Alternatively, collar 502 may be of a clamshell type design having a hinge and a snap lock for engagement about IV pole 1 and anti-rotation key 500.

Figure 18A:
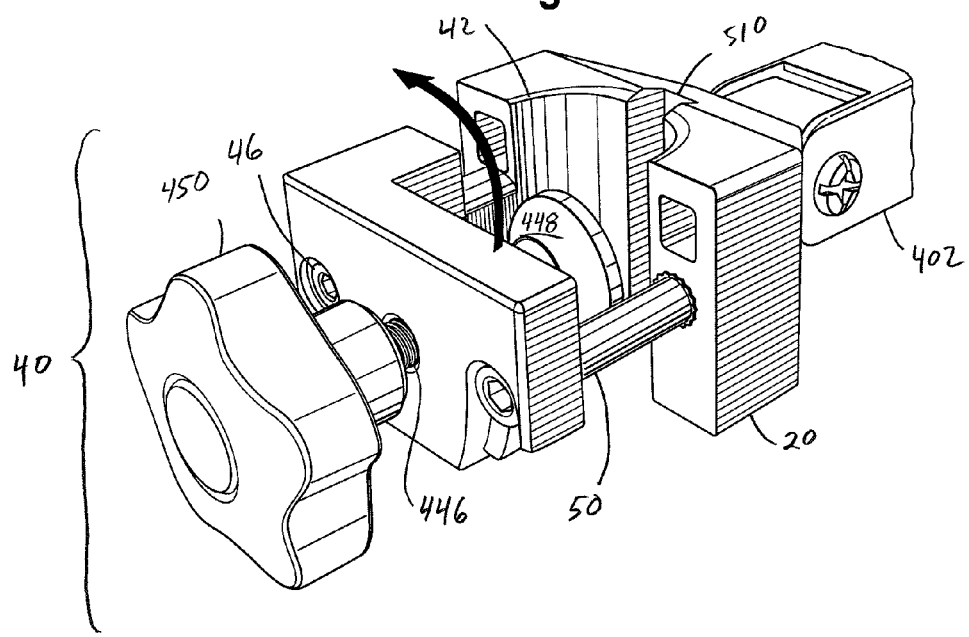
Figure 18B:
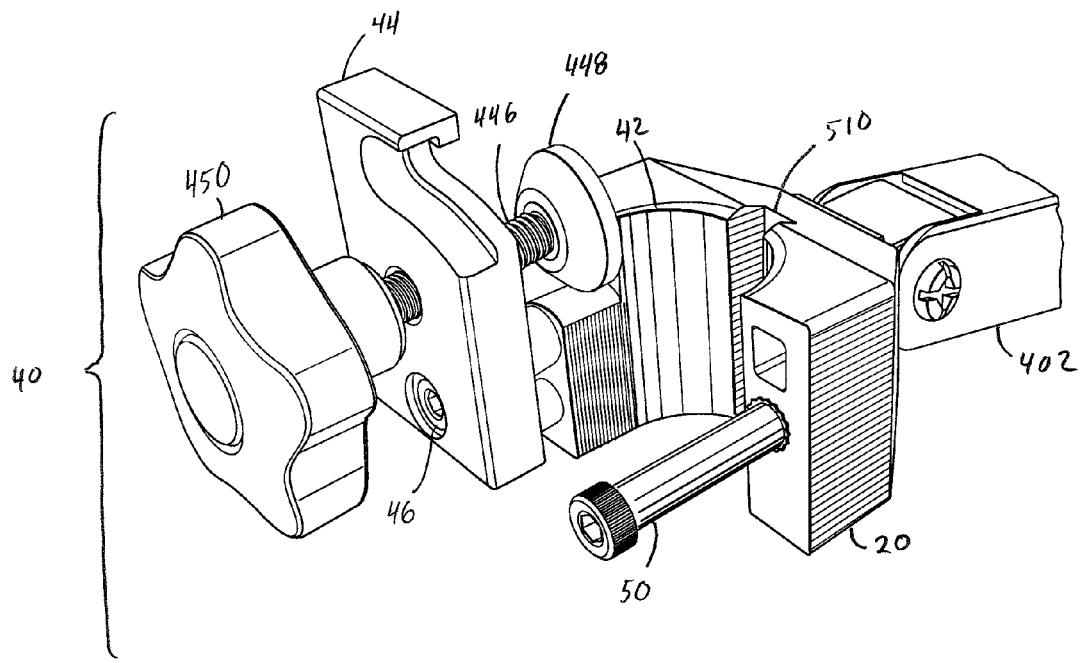

Referring now to FIGS. 18A and 18B, the anti-rotation key 500 shown in FIGS. 16 and 17 is configured for cooperation with a keyway 510 provided in the body 20 within attachment recess 42. The anti rotation key 500 attached to IV pole 1 cooperates with keyway 510 to prevent IV pole 1 from rotating during transit, and thus minimizes tangling of IV lines and problems associated therewith.

Referring to FIGS. 19 and 20, another embodiment of the present disclosure includes a body 520 including an integral mounting portion 530. Mounting portion 530 is configured as an integral flange extending from body 520. Mounting portion 530 includes one or more mounting apertures 532 configured to accommodate a fastener (not shown) for mounting to a piece of movable medical equipment 2 such as a hospital bed. Mounting portion 530 may be secured to movable medical equipment 2 by fasteners positioned within mounting apertures 532 such as screws, bolts, rivets, and the like.

The embodiment shown in FIGS. 19 and 20 further includes a collapsible handle assembly 550. Handle assembly 550 includes a grip 552 attached to a shaft 554 at a first end 556. A pin 558 is disposed through the shaft 554 at a second end 560. Pin 558 is configured to engage a slot 562 provided in body 520. In the exemplary embodiment, slot 562 is oriented substantially horizontal. A notch 564 is provided within the body 520 to receive the second end 560 of shaft 554. Slot 562 may include a drop slot 566 located toward the front end. Drop slot allows pin 558 to drop down when handle assembly 550 is moved forward, providing clearance between the second end 560 of shaft 554 and body 520, allowing handle assembly to be rotated upwardly as shown by the broken lines in FIG. 20.

In operation, this embodiment provides dual function as an IV pole clamp and as a handle for pulling a piece of movable medical equipment 2. Referring again to FIGS. 19 and 20, when it is desired to secure an IV pole to movable medical equipment 2, handle assemble 550 is slid backwardly in slot 562 so as to clear attachment recess 42 and keyway 510, allowing for an IV pole (not shown) to be received within attachment recess 42. When an IV pole is not secured by this exemplary embodiment, such as, for example, when an empty hospital bed is being transported to storage, handle assembly 550 may be moved forward in slot 562, until pin 558 falls into drop slot 566, allowing handle assembly to be rotated upwardly as shown in FIG. 20 and used to pull movable medical equipment 2.

A feature of the device of the present disclosure is that the device may be fabricated from a number of materials including aluminum, steel, stainless steel, plastic, alloys, etc. Particularly, since it is envisioned that one use of the present device is within the healthcare arena, it is important that the device is fabricated from a latex-free material because of complications that can develop as a result of latex allergies. Also, because of the use of electrical equipment in hospitals and other healthcare settings, another aspect of the present disclosure is that it may be fabricated from an electrically insulating material to protect the patient in the event of an equipment malfunction.

While preferred embodiments of the present invention are shown and described, it is envisioned that those skilled in the art may devise various modifications of the present invention without departing from the spirit and scope of the appended claims.

I claim:

1. A clamping device for attaching a piece of first movable medical equipment to a piece of second movable medical equipment comprising:

a body;

a mounting portion connected to the body, wherein the mounting portion is integrally connected to the body and the mounting porting is an integral flange extending outwardly from the body, wherein the integral flange includes one or more mounting apertures configured to receive fasteners for affixing the integral flange to the piece of second movable medical equipment;

an attachment portion connected to the body opposite the mounting portion, the attachment portion comprising:
- an attachment recess disposed within said body for receiving the piece of first movable equipment, the attachment recess including a keyway configured to receive an anti-rotation key affixed to the first piece of movable medical equipment, and
- a latch plate rotatably attached to said body at a pivot disposed on one side of said attachment recess, wherein said latch plate may be pivotally disposed between an open position and a closed position,
- said latch plate having a notch configured to cooperate with a latch pin when said latch plate is disposed in the closed position, said latch pin being attached to said body on a side of said attachment recess opposite said pivot,
- said latch plate further having a groove disposed on an edge thereof proximate to said pivot, wherein said groove is configured to cooperate with a stop attached to said body when said latch plate is in the open position,
- said latch plate further having an attachment lock disposed within said latch plate, said attachment lock being configured to produce a force against the piece of first moveable equipment with said latch plate being in the closed position, wherein the attachment lock comprises a screw disposed through and threadedly engaged with the latch plate, the screw having an inboard end and an outboard end, wherein a pad configured to engage the piece of first movable medical equipment is disposed on the inboard end of the screw and an adjustment knob is disposed on the outboard end of the screw.

2. A clamping device for attaching a piece of first movable medical equipment to a piece of second movable medical equipment comprising:
- a body;
- a mounting portion connected to the body, wherein the mounting portion comprises a channel defined by a web and a flange, a set screw having an inboard end and an outboard end being disposed through and threadedly engaged with the flange, an adjustment knob being disposed on the outboard end of the set screw and a pad being disposed on the inboard end of the set screw;
- an attachment portion connected to the body opposite the mounting portion, the attachment portion comprising:
  - an attachment recess disposed within said body for receiving the piece of first movable equipment, the attachment recess including a keyway configured to receive an anti-rotation key affixed to the first piece of movable medical equipment, and
  - a latch plate rotatably attached to said body at a pivot disposed on one side of said attachment recess, wherein said latch plate may be pivotally disposed between an open position and a closed position,
  - said latch plate having a notch configured to cooperate with a latch pin when said latch plate is disposed in the closed position, said latch pin being attached to said body on a side of said attachment recess opposite said pivot,
  - said latch plate further having a groove disposed on an edge thereof proximate to said pivot wherein said groove is configured to cooperate with a stop attached to said body when said latch plate is in the open position,
  - said latch plate further having an attachment lock disposed within said latch plate, said attachment lock being configured to produce a force against the piece of first moveable equipment with said latch late being in the closed position.

3. A clamping device for attaching a piece of first movable medical equipment to a piece of second movable medical equipment comprising:
- a body;
- a mounting portion connected to the body, wherein the mounting portion comprises a channel defined by a web and a flange, a set screw having an inboard end and an outboard end being disposed through and threadedly engaged with the flange, an adjustment knob being disposed on the outboard end of the set screw and a pad being disposed on the inboard end of the set screw, wherein the web includes an arcuate mounting recess disposed between a pair of flats;
- an attachment portion connected to the body opposite the mounting portion, the attachment portion comprising:
  - an attachment recess disposed within said body for receiving the piece of first movable equipment, the attachment recess including a keyway configured to receive an anti-rotation key affixed to the first piece of movable medical equipment, and
  - a latch plate rotatably attached to said body at a pivot disposed on one side of said attachment recess, wherein said latch plate may be pivotally disposed between an open position and a closed position,
  - said latch plate having a notch configured to cooperate with a latch pin when said latch plate is disposed in the closed position, said latch pin being attached to said body on a side of said attachment recess opposite said pivot,
  - said latch plate further having a groove disposed on an edge thereof proximate to said pivot, wherein said groove is configured to cooperate with a stop attached to said body when said latch plate is in the open position,
  - said latch plate further having an attachment lock disposed within said latch plate, said attachment lock being configured to produce a force against the piece of first moveable equipment with said latch plate being in the closed position.

* * * * *

UNITED STATES PATENT AND TRADEMARK OFFICE
CERTIFICATE OF CORRECTION

PATENT NO. : 8,459,602 B2
APPLICATION NO. : 12/780274
DATED : June 11, 2013
INVENTOR(S) : Arnold Herskovic Page 1 of 1

It is certified that error appears in the above-identified patent and that said Letters Patent is hereby corrected as shown below:

In the Claims

Claim 1, col. 10, line 65, delete the word "porting" and insert in its place the word --portion--.

Claim 2, col. 12, line 7, add a --,-- after the word "pivot".

Claim 2, col. 12, line 14, delete the word "late" and insert in its place the word --plate--.

Signed and Sealed this
Twentieth Day of August, 2013

Teresa Stanek Rea
*Acting Director of the United States Patent and Trademark Office*